(12) United States Patent
Simon et al.

(10) Patent No.: US 9,254,153 B2
(45) Date of Patent: Feb. 9, 2016

(54) HIP FRACTURE DEVICE WITH STATIC LOCKING MECHANISM ALLOWING COMPRESSION

(71) Applicant: Stryker Trauma GmbH, Schönkirchen (DE)

(72) Inventors: Bernd Simon, Kiel (DE); Jakob Kemper, Santiago (CL); Carsten Hoffmann, Mönkeberg (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 14/172,161

(22) Filed: Feb. 4, 2014

(65) Prior Publication Data

US 2014/0148861 A1 May 29, 2014

Related U.S. Application Data

(62) Division of application No. 12/082,689, filed on Apr. 11, 2008, now Pat. No. 8,734,494.

(60) Provisional application No. 60/925,457, filed on Apr. 19, 2007.

(51) Int. Cl.
*A61B 17/70* (2006.01)
*A61B 17/04* (2006.01)
(Continued)

(52) U.S. Cl.
CPC ............... *A61B 17/74* (2013.01); *A61B 17/746* (2013.01); *A61B 17/8042* (2013.01); *A61B 17/8685* (2013.01)

(58) Field of Classification Search
CPC ...... A61B 17/70; A61B 17/04; A61B 17/746; A61B 17/8685

USPC ............ 606/65–66, 280–299, 104, 300–331, 606/246–279
See application file for complete search history.

(56) References Cited

U.S. PATENT DOCUMENTS 2,397,545 A 4/1946 Hardinge
2,612,159 A 9/1952 Collison
(Continued)

FOREIGN PATENT DOCUMENTS

DE 918531 C 9/1954
DE 931431 C 8/1955
(Continued)

OTHER PUBLICATIONS

Osteon News 39 Brouchre, Comprehension Hip Screw.

*Primary Examiner* — Christopher Beccia
(74) *Attorney, Agent, or Firm* — Lerner, David, Littenberg, Krumholz & Mentlik, LLP (57) ABSTRACT

In one embodiment, the present invention is a method of fusing fractures of a femoral neck using a bone plate including the steps of: placing a bone plate on the femur; inserting an assembly of a bone screw and a locking ring in an opening in the plate; simultaneously threading the locking ring and the bone screw in the femur; threading the bone screw in the femur to compress the fracture; creating a space between the locking ring and the bone screw; and allowing the bone screw to move towards the locking ring when the femur is loaded. In another embodiment, the present invention is a bone plating system including a bone plate having a plurality of openings; at least one bone screw capable of being received through the opening and into a bone; at least one end cap fixedly insertable in the opening; and a layer of polymeric material interposed between the end cap and the top of the head.

2 Claims, 5 Drawing Sheets

(51) Int. Cl.
*A61B 17/74* (2006.01)
*A61B 17/80* (2006.01)
*A61B 17/86* (2006.01)

(56) References Cited

U.S. PATENT DOCUMENTS

| | | |
|---|---|---|
| 2,628,614 A | 2/1953 | Briggs |
| 2,631,584 A | 3/1953 | Purifacto |
| 2,702,543 A | 2/1955 | Pugh et al. |
| 2,761,444 A | 9/1956 | Luck |
| 2,801,631 A | 8/1957 | Charnley |
| 2,834,342 A | 5/1958 | Yost |
| 3,029,811 A | 4/1962 | Yost |
| 3,107,666 A | 10/1963 | Cecere et al. |
| 3,374,786 A | 3/1968 | Callender |
| 4,236,512 A | 12/1980 | Aginsky |
| 4,432,358 A | 2/1984 | Fixel |
| 4,438,762 A | 3/1984 | Kyle |
| 4,465,065 A | 8/1984 | Gotfried |
| 4,488,543 A | 12/1984 | Tornier |
| 4,612,920 A | 9/1986 | Lower |
| 4,621,629 A | 11/1986 | Koeneman |
| 4,628,923 A | 12/1986 | Medoff |
| 4,657,001 A | 4/1987 | Fixel |
| 4,827,917 A | 5/1989 | Brumfield |
| 4,940,467 A | 7/1990 | Tronzo |
| RE33,348 E | 9/1990 | Lower |
| 5,007,910 A | 4/1991 | Anapliotis et al. |
| 5,032,125 A | 7/1991 | Durham et al. |
| 5,041,116 A | 8/1991 | Wilson |
| 5,116,336 A | 5/1992 | Frigg |
| 5,122,133 A | 6/1992 | Evans |
| 5,167,663 A | 12/1992 | Brumfield |
| 5,217,462 A | 6/1993 | Asnis et al. |
| 5,429,641 A | 7/1995 | Gotfried |
| 5,437,674 A | 8/1995 | Worcel et al. |
| 5,514,138 A | 5/1996 | McCarthy |
| 5,534,027 A | 7/1996 | Hodorek |
| 5,578,034 A | 11/1996 | Estes |
| 5,735,853 A | 4/1998 | Olerud |
| 5,743,912 A | 4/1998 | Lahille et al. |
| 5,827,285 A | 10/1998 | Bramlet |
| 5,871,485 A | 2/1999 | Rao et al. |
| 5,893,850 A | 4/1999 | Cachia |
| 5,899,906 A | 5/1999 | Schenk |
| 5,904,683 A | 5/1999 | Pohndorf et al. |
| 5,931,838 A | 8/1999 | Vito |
| 5,976,139 A | 11/1999 | Bramlet |
| 6,004,327 A | 12/1999 | Asnis et al. |
| 6,139,552 A | 10/2000 | Horiuchi |
| 6,183,474 B1 | 2/2001 | Bramlet et al. |
| 6,187,007 B1 | 2/2001 | Frigg et al. |
| 6,224,606 B1 | 5/2001 | Horiuchi |
| 6,235,033 B1 | 5/2001 | Brace et al. |
| 6,383,227 B1 | 5/2002 | Baroud et al. |
| 6,402,755 B1 | 6/2002 | Pisharodi |
| 6,454,769 B2 | 9/2002 | Wagner et al. |
| 6,468,278 B1 | 10/2002 | Muckter |
| 6,511,481 B2 | 1/2003 | von Hoffmann et al. |
| 6,527,776 B1 | 3/2003 | Michelson |
| 6,533,789 B1 | 3/2003 | Hall, IV et al. |
| 6,592,586 B1 | 7/2003 | Michelson |
| 6,595,993 B2 | 7/2003 | Donno et al. |
| 6,599,290 B2 | 7/2003 | Bailey et al. |
| 6,602,255 B1 | 8/2003 | Campbell et al. |
| 6,620,163 B1 | 9/2003 | Michelson |
| 6,632,224 B2 | 10/2003 | Cachia et al. |
| 6,645,209 B2 | 11/2003 | Hall, IV et al. |
| 6,679,883 B2 | 1/2004 | Hawkes et al. |
| 6,685,706 B2 | 2/2004 | Padget et al. |
| 6,717,214 B2 | 4/2004 | Pettruzello et al. |
| 6,887,243 B2 | 5/2005 | Culbert |
| 6,890,333 B2 | 5/2005 | von Hoffmann et al. |
| 6,902,567 B2 | 6/2005 | Del Medico |
| 6,908,465 B2 | 6/2005 | von Hoffmann et al. |
| 6,942,668 B2 | 9/2005 | Padget et al. |
| 6,951,561 B2 | 10/2005 | Warren et al. |
| 6,997,243 B2 | 2/2006 | Hsu |
| 7,001,389 B1 | 2/2006 | Navarro et al. |
| 7,048,739 B2 | 5/2006 | Konieczynski et al. |
| 7,070,601 B2 | 7/2006 | Culbert et al. |
| 7,081,117 B2 | 7/2006 | Bono et al. |
| 7,105,029 B2 | 9/2006 | Doubler et al. |
| 7,135,023 B2 | 11/2006 | Watkins et al. |
| 7,135,028 B2 | 11/2006 | Sugimura et al. |
| 7,273,481 B2 | 9/2007 | Lombardo et al. |
| 7,326,211 B2 | 2/2008 | Padget et al. |
| 7,556,629 B2 | 7/2009 | von Hoffmann et al. |
| 7,699,880 B2 | 4/2010 | Orbay et al. |
| 7,846,190 B2 | 12/2010 | Ball |
| 7,935,137 B2 | 5/2011 | Gorhan et al. |
| 7,942,913 B2 | 5/2011 | Ziolo et al. |
| 7,972,366 B2 | 7/2011 | Richelsoph et al. |
| 2001/0049528 A1 | 12/2001 | Kubota |
| 2002/0049445 A1 | 4/2002 | Hall et al. |
| 2002/0143333 A1 | 10/2002 | von Hoffmann et al. |
| 2002/0143334 A1 | 10/2002 | Hoffmann et al. |
| 2002/0198527 A1 | 12/2002 | Muckter |
| 2003/0069582 A1 | 4/2003 | Culbert |
| 2003/0083660 A1 | 5/2003 | Orbay |
| 2003/0097132 A1 | 5/2003 | Padget et al. |
| 2003/0187440 A1 | 10/2003 | Richelsoph et al. |
| 2004/0019353 A1 | 1/2004 | Freid et al. |
| 2004/0030339 A1 | 2/2004 | Wack et al. |
| 2004/0030340 A1 | 2/2004 | Pisharodi |
| 2004/0087951 A1* | 5/2004 | Khalili ........................... 606/69 |
| 2004/0127896 A1 | 7/2004 | Lombardo et al. |
| 2004/0127899 A1 | 7/2004 | Konieczynski et al. |
| 2004/0181222 A1 | 9/2004 | Culbert et al. |
| 2004/0199162 A1 | 10/2004 | von Hoffmann et al. |
| 2004/0220572 A1 | 11/2004 | Michelson |
| 2004/0225289 A1 | 11/2004 | Biedermann et al. |
| 2004/0236335 A1 | 11/2004 | Michelson |
| 2005/0015089 A1 | 1/2005 | Young et al. |
| 2005/0015131 A1 | 1/2005 | Fourcault et al. |
| 2005/0096657 A1 | 5/2005 | Autericque et al. |
| 2005/0131411 A1 | 6/2005 | Culbert |
| 2005/0143735 A1 | 6/2005 | Kyle |
| 2005/0143742 A1 | 6/2005 | Porcher |
| 2005/0228386 A1 | 10/2005 | Ziolo et al. |
| 2005/0234457 A1 | 10/2005 | James et al. |
| 2005/0251137 A1 | 11/2005 | Ball |
| 2005/0251142 A1 | 11/2005 | Hoffmann et al. |
| 2005/0277922 A1* | 12/2005 | Trieu et al. .................. 606/61 |
| 2006/0142770 A1* | 6/2006 | Capanni ........................ 606/73 |
| 2006/0155281 A1 | 7/2006 | Kaup et al. |
| 2006/0167456 A1 | 7/2006 | Johnston et al. |
| 2006/0214606 A1 | 9/2006 | Kimura et al. |
| 2006/0217711 A1 | 9/2006 | Stevens et al. |
| 2006/0241606 A1 | 10/2006 | Vachtenberg et al. |
| 2006/0241616 A1 | 10/2006 | Konieczynski et al. |
| 2006/0241618 A1 | 10/2006 | Gasser et al. |
| 2007/0162011 A1 | 7/2007 | Leyden et al. |
| 2007/0260248 A1 | 11/2007 | Tipirneni |
| 2008/0119855 A1 | 5/2008 | Hoegerle et al. |
| 2008/0177330 A1 | 7/2008 | Ralph et al. |
| 2008/0255559 A1* | 10/2008 | Leyden et al. ................. 606/62 |
| 2008/0269752 A1 | 10/2008 | Simon et al. |
| 2008/0275508 A1 | 11/2008 | Haidukewych |
| 2009/0254129 A1 | 10/2009 | Tipirneni et al. |
| 2009/0264885 A1 | 10/2009 | Grant et al. |
| 2010/0174285 A1 | 7/2010 | Probe |
| 2010/0312245 A1 | 12/2010 | Tipirneni et al. |

FOREIGN PATENT DOCUMENTS

| | | |
|---|---|---|
| DE | 1225812 B | 9/1966 |
| DE | 8900121 U1 | 2/1990 |
| DE | 195 05 609 A1 | 8/1996 |
| DE | 19504115 A1 | 8/1996 |
| DE | 29709725 U1 | 8/1997 |
| DE | 29908360 U1 | 9/2000 |
| DE | 102005007674 B4 | 2/2007 |
| EP | 0482875 A1 | 4/1992 |

(56) References Cited

FOREIGN PATENT DOCUMENTS

| | | |
|---|---|---|
| EP | 0 321 170 B1 | 11/1994 |
| EP | 0617927 B1 | 1/1999 |
| EP | 0668059 B1 | 1/2000 |
| EP | 807420 B1 | 7/2002 |
| EP | 988833 B1 | 10/2003 |
| EP | 1486175 B1 | 11/2009 |
| FR | 2674119 A1 | 9/1992 |
| FR | 2832308 B1 | 9/2004 |
| JP | 06125918 A | 5/1994 |
| JP | 06245941 A | 9/1994 |
| JP | 8322848 A | 12/1996 |
| JP | 2001149379 A | 6/2001 |
| JP | 2002-360599 A | 12/2002 |
| WO | 0067652 B1 | 11/2000 |
| WO | 01/03592 A1 | 1/2001 |
| WO | 2004006792 A1 | 1/2004 |
| WO | 2006087159 A1 | 8/2006 |
| WO | 2007138062 A1 | 12/2007 |

* cited by examiner

HIP FRACTURE DEVICE WITH STATIC LOCKING MECHANISM ALLOWING COMPRESSION

CROSS-REFERENCE TO RELATED APPLICATION

The present application is a divisional of U.S. patent application Ser. No. 12/082,689, filed Apr. 11, 2008, which claims the benefit of the filing date of U.S. Provisional Patent Application No. 60/925,457 filed Apr. 19, 2007, the disclosure of which is hereby incorporated herein by reference.

BACKGROUND OF THE INVENTION

1. Field of The Invention

The present invention relates generally to an apparatus and method for the treatment of fractures of the proximal femur including the neck of the femur and the intertrochantric region.

2. Brief Description of the Prior Art

In treatment of the fracture of the femoral neck it is necessary to maintain angular stability of the head fragment to maintain an anatomical reduction postoperatively. It is also desirable to compress fracture site intra-operatively and then to stabilize the bone fragments by not allowing any further axial or angular movement. Since axial movement of the bone fragment resulting in shortening of the neck of the femur will result in reduced physical functioning, particularly in younger patients, it is desirable to stabilize the fracture postoperatively.

Many locking plates are available that allow stabilization of bone fragments. Conventional locking plates (also known as bone plates) have a plate that is attached to the fragments of the fractured bone via screws that are inserted in the bone through screw holes in the plate. The screws of the conventional locking plates have threads on the head portion in addition to the threads on the shaft. The threads on the head portion have a greater core diameter than the threads on the shaft but both threads have same pitch. When the screw is advanced in the bone and the head of the screw is in the screw hole of the bone plate, the threads on the screw head engage matching threads in the screw hole. This locks the screw in place and prevents it from moving in the axial direction post operatively. However, such bone plate system cannot be used to compress the fracture site. In another conventional bone plate system used for femoral neck fracture a compression screw is used. The compression screw head does not have the threads and therefore may be rotated further after its head has reached the final axial position thereby compressing the fracture site. A separate end cap is then screwed in the compression screw hole of the bone plate to prevent the screw from moving back in the axial direction.

These bone plate systems require a separate step of installing an end cap to prevent post operative axial movement of the screw. Therefore, there is a need for further improvement in bone plate systems to provide an easy to use plate system that facilitates intra-operative compression and at the same time provides angular and axial stability post operatively.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

SUMMARY OF THE INVENTION

The present invention provides a bone plate for use with fractures of the femur. Screws attach the bone plate to the femur. The compression screws that are inserted in the neck of the femur may be parallel to the axis of the neck of the femur. Inserting the bone screws in the neck region of the femur provides compression and angular and rotational stability to the head of the femur. Cortical interlocking type screws may be used in a distal portion of the bone plate in the subtrochantric shaft region of the femur. The compression screws stabilize bone fragments when used with end caps and prevent the shortening of the femoral neck resulting in improved postoperative function of the hip. The end cap may be inserted in a threaded plate hole and contact the top of each screw. A polymer buffer may be placed in the screw hole between the end cap and the head of the compression screw. The polymer buffer may allow small movement of the screw.

In use, the compression bone screw is inserted in the screw hole and screwed into the neck of the femur until the underside of the bone screw sits on the flat face formed in screw hole. Next, the screw is rotated further to apply compression to the fracture site. Once the desired amount of compression is applied, the end cap is inserted in screw hole. The end cap prevents the screw from moving back in the axial direction.

In another embodiment, a compression screw having a different head design is used with a split locking ring. The locking ring has a smooth circular outer surface that fits in the screw hole. The inner surface of the locking ring has a saw blade like or similarly functioning geometry. The saw blade geometry on the inner surface is preferably asymmetric. The compression screw head has a saw blade geometry that can mate with the saw blade geometry on the inner surface of the locking ring.

In use, the screw and the split locking ring are assembled together and inserted into the screw hole. The assembly of the screw and the locking ring is then screwed into the bone using a dedicated insertion instrument that holds and rotates the screw and the locking ring simultaneously. When the head of the screw reaches the terminal axial position in the screw hole, both the screw and the locking ring can be rotated further to apply compression to the fracture site. After the compression is applied, the screw alone is turned. The locking ring is thereby clamped between the head of screw and the bone plate. This results in fixing the screw in place such that the screw can not back out in axial direction.

In yet another embodiment, a compression screw having a different head design is used with a locking ring. The locking ring has a threaded circular outer surface that fits in the screw hole. The top wall of the locking ring projects towards the center of the screw hole and has a hexagonal internal periphery. The bottom surface of the top wall has ridges. The screw has a head that has an outer peripheral surface that slidably fits into the locking ring. The top surface of the head of the screw has depressions that correspond to the ridges. Thus, when the screw is assembled in locking ring, the ridges sit in the depressions. The top surface of the screw head also has a hexagonal depression to allow engagement of a suitable screw driver.

In use, the compression screw and the locking ring are assembled together and inserted into the screw hole. The assembly of the screw and the locking ring is then screwed into the bone using a dedicated insertion instrument that holds and rotates the screw and the locking ring simultaneously. When the head of the screw reaches the terminal axial position in the screw hole, the screw can be rotated further to apply compression to the fracture site. When the screw is rotated further the ridges loose contact with the depressions. This forms a small gap of approximately 0.1-0.4 millimeters between the screw and the locking ring. As soon as the body weight is applied post-operatively, the femoral head fracture fragment presses the screw back to the lateral side until the movement is stopped by the locking ring. The polymer buffer may also be used with any of the above described embodiments.

In one aspect the present invention provides a bone plating system having a bone plate having a plurality of openings. The system includes at least one bone screw for insertion in the opening and into a bone and having a head. Depressions are formed on a top surface of the head, and a locking ring adapted to attach to the head and having ridges that have shape complimentary to the depressions is provided. The locking ring fits in the depressions when the locking ring is attached to the head. The locking ring and the bone screw are assembly together and simultaneously inserted in the opening using a dedicated instrument.

In another aspect, a bone plating system includes a bone plate having a plurality of openings. The system also has at least one bone screw capable of being received through the opening and into a bone. The head of the bone screw has an asymmetric saw blade geometry formed on the periphery. A locking ring having an asymmetric saw blade geometry matching the asymmetric saw blade geometry formed on the periphery of the head is provided. The locking ring and the bone screw are assembly together such that the saw blade geometry on the locking ring is in engagement with the saw blade geometry on the head, and the assembly is inserted in the opening using a dedicated instrument.

In yet another aspect, a bone plating system includes a bone plate having a plurality of openings and at least one bone screw capable of being received through the opening and into a bone. The bone screw having a head adapted for fitting in the opening when the bone screw is fully inserted in the bone, the head of the bone screw and the opening in the bone plate having complementary shape such that the bone screw when seated in the opening has angular stability. At least one end cap is fixedly inserted in the opening, and a layer of polymeric material is interposed between the end cap and the top of the head such that the compression of the polymeric material would allow slight axial movement of the screw.

In yet another aspect, a method of fusing fractures of femoral neck using a bone plate is disclosed. The method includes placing a bone plate on the femur, and inserting an assembly of a bone screw and a locking ring in an opening in the plate. Thereafter, simultaneously threading the locking ring and the bone screw in the femur and further threading the bone screw in the femur to compress the fracture. A space is created between the locking ring and the bone screw allowing the bone screw to move towards the locking ring when the joint is loaded.

DETAILED DESCRIPTION

Figure 1:
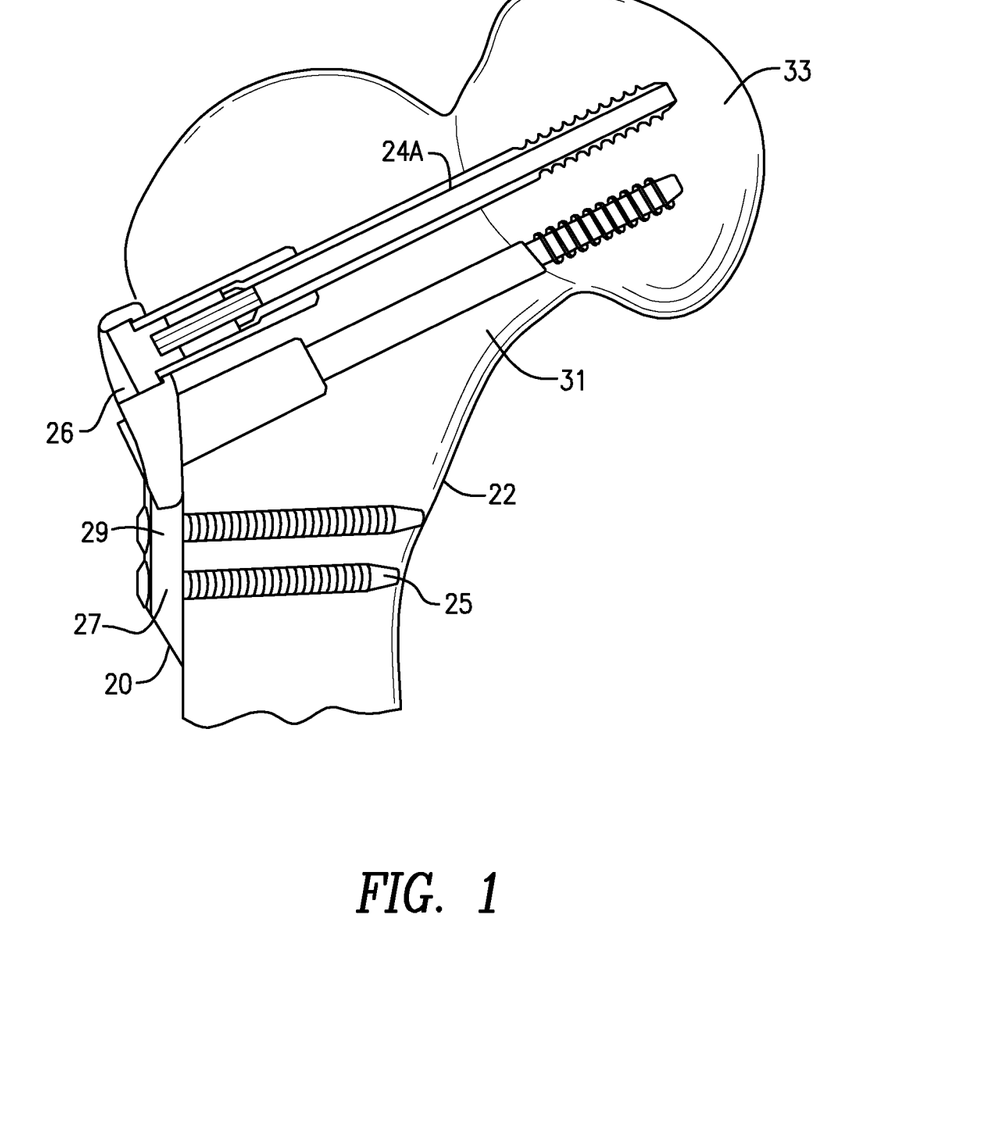
FIG. 1 is an anterior elevation view of a bone plate mounted on a femur.
Figure 1A:
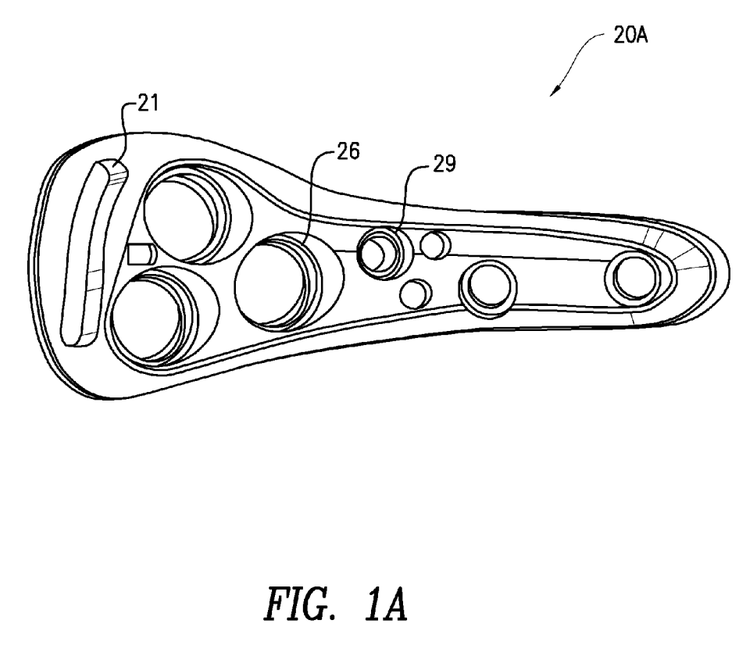
FIG. 1A shows another embodiment of a bone plate that may be mounted on the femur.

FIG. 1 shows a bone plate 20 mounted on a femur 22. Any one of the compression screws disclosed hereafter may be used with the bone plate 20. In FIG. 1, compression screws 24A attach the bone plate 20 to the head 33 and neck 31 of femur 22. Screws 24A may be used to attach bone plate 20 to the femur via screw holes 26 in plate 20. Cortical screws 25 may be used to attach a distal portion 27 of bone plate 20 to the subtrochantric shaft of the femur 22. In the preferred embodiment these are locking screws. The compression screw 24A may provide angular and axial stability to the fractured bone pieces. The compression screws 24A may be cannulated or non-cannulated. The compression screws 24A may also provide rotational stability. Rotational stability may be achieved by inserting at least two compression screws 24A through the screw holes 26 and into the neck 31 of the femur 22. The compression screws 24A that are inserted in the neck 31 of the femur 22 may be parallel to the axis of the neck 31 of the femur 22. Cortical interlocking type screws 25 may be used in plate holes 29 in the subtrochantric shaft region of the femur 22. The cortical interlocking screws 25 may have threads (not seen in the figures) on the periphery of the head portion for engaging threads in hole 29. The cortical interlocking type screws 25 may be used to prevent the backout of the screws 25 and the bone plate 20. The compression screws 24A stabilize the neck fracture head fragment and thereby prevent the shortening of the femoral neck 31 resulting in improved post-operative function of the hip. FIG. 1A shows a plate 20A. Plate 20A is a variation of design of plate 20, and includes a slot 21. A guide wire may be inserted through slot 21 and into the head 33 of femur 22. The guide wire may be used to position the plate 20A in a desired alignment on the surface of the femur 22. Any one of the compression screws disclosed hereafter may be used with the bone plate 20A.

Figure 2:
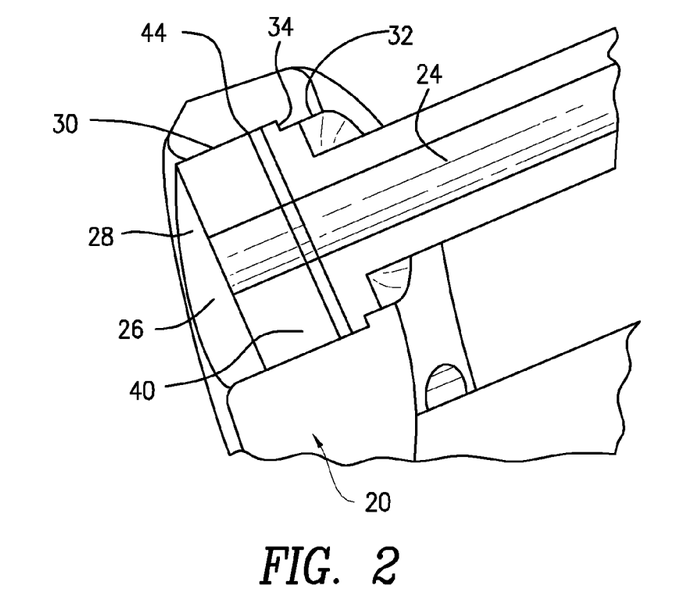
FIG. 2 shows an isometric sectional view of a screw hole in the bone plate of FIG. 1 with a bone screw and an end cap inserted therein.

FIG. 2 shows the screw hole 26 in the bone plate 20 with bone compression screw 24 and an end cap 28 inserted in the screw hole 26. The bone compression screw 24 may be a cannulated screw. However, non-cannulated screws may also be used. In a preferred embodiment, the screw hole 26 has a first threaded section 30 having a larger diameter and a second section 32 having a smaller diameter. A flat face 34 is formed at the junction of the first threaded section 30 and the second section 32. Threads (not seen in the figures) may be formed on all or portion of the inner periphery of the first threaded section 30. Inserting one bone compression screw 24 in the neck region of the femur 22 provides angular stability to the head 33 of the femur 22. One or two or three or more bone compression screws 24 may be inserted in the neck region of the femur 22. Inserting more than one bone compression screw 24 provides rotational stability to the head 33 of the femur 22. An end cap 40 may be inserted in screw hole 26 on top of each compression screw 24. A polymer buffer 44 may be placed in the screw hole 26 between the end cap 40 and the head of the compression screw 24. The polymer buffer 44 may allow small movement of the compression screw 24.

In use, the bone compression screw 24 is inserted in the screw hole 26 and screwed into the neck 31 of the femur 22 until the underside of the bone compression screw 24 sits on the flat face 34 formed in screw hole 26. Next, the compression screw 24 is rotated further to apply compression to the fracture site. Once desired amount of compression is applied, the end cap 40 is inserted in screw hole 26. End cap 40 has threads (not seen in the figures) on its periphery that mate with the threads in the screw hole 26. End cap 40 is screwed into the screw hole 26 till its bottom is on top of the top surface of the head of the compression screw 24 that was previously installed in that screw hole 26. Thus, the end cap 40 prevents the compression screw 24 from moving back in the axial direction. Optionally, the polymer buffer 44 may be placed over the compression screw 24 prior to installing the end cap 40. Cortical bone screw 25 are also installed in screw holes 29 and screwed into the subtrochantric shaft region of the femur 22. The screws 24 and 25 stabilize the bone fracture. The end cap 40 and the bone plate 20 also provide angular stability.

Figure 3:
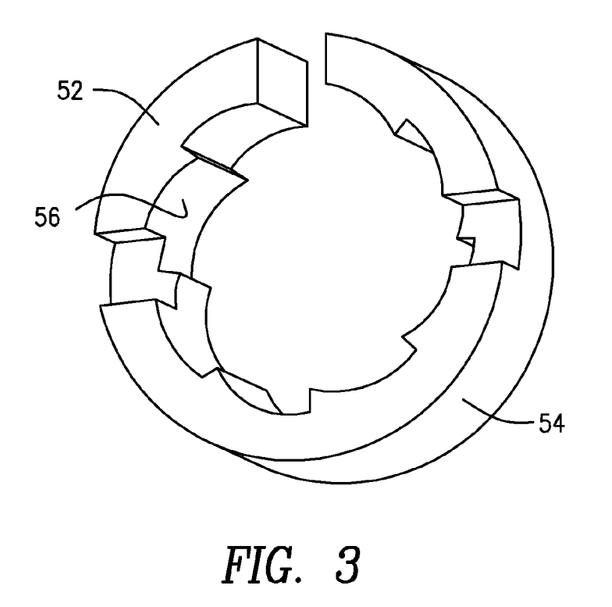
FIG. 3 is an isometric view of a first locking ring embodiment.
Figure 4:
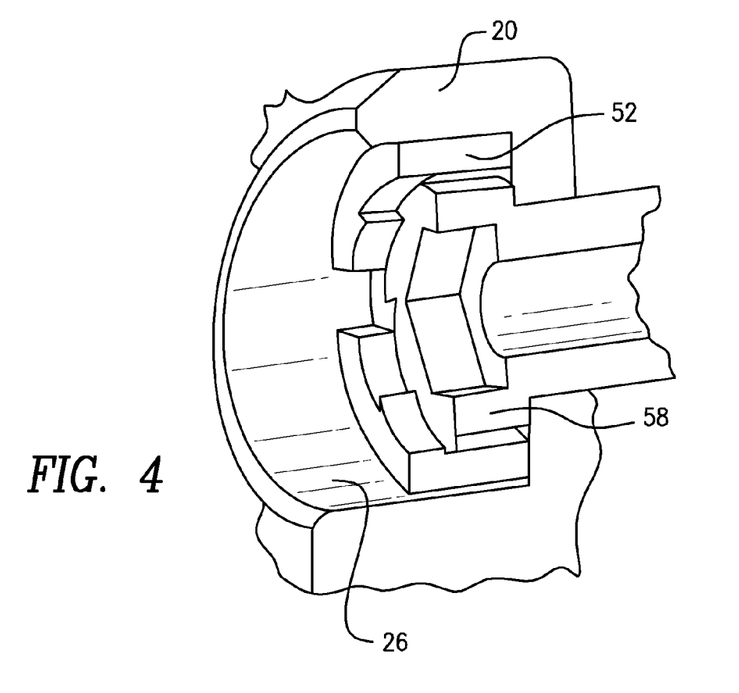
FIG. 4 shows a sectional view of the bone plate of FIG. 1 with a locking ring and a screw installed therein.
Figure 5:
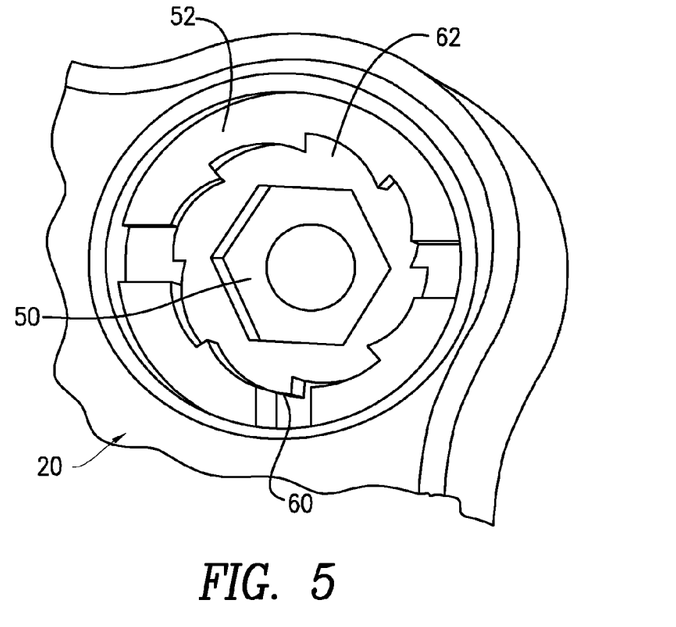
FIG. 5 is a lateral view of a portion of a bone plate assembly showing the bone plate, a screw and the locking ring of FIG. 3.

In another embodiment a compression screw 50 of a different head design is used with a split locking ring 52. FIG. 3 shows the locking ring 52. FIG. 4 shows a cross sectional view of the bone plate 20 with the locking ring 52 and the compression screw 50 installed therein. FIG. 5 is a top view of a portion of a bone plate assembly showing the bone plate 20, the compression screw 50 and the locking ring 52. The locking ring 52 has a smooth circular outer surface 54 that fits in the screw hole 26. The inner surface 56 of the locking ring 52 has a saw blade like geometry. The saw blade geometry on the inner surface 56 is asymmetric. The compression screw 50 has a head 58 that has an outer peripheral surface 60 with a saw blade geometry that can mate with the saw blade geometry on the inner surface 56 of the locking ring 52. The top surface 62 of the screw head 58 has a hexagonal depression to allow engagement of a suitable screw driver. Other known shapes for the depression and corresponding screwdriver may also be used.

In use, the compression screw 50 and the split locking ring 52 are assembled together and inserted into the screw hole 26. The assembly of the compression screw 50 and the locking ring 52 is then screwed into the bone using a dedicated insertion instrument that holds and rotates the compression screw 50 and the locking ring 52 simultaneously. When the head of the compression screw 50 reaches the terminal axial position in the screw hole 26, both the compression screw 50 and the locking ring 52 can be rotated further to apply compression to the fracture site. After the compression is applied, the compression screw 50 alone is turned. This makes the compression screw 50 rotate in relation to locking ring 52 which results in partial disengagement of saw blade geometry on the inner surface 56 of the locking ring 52 from the saw blade geometry on the outer peripheral surface 60. Since the saw blade geometries on both these surfaces are asymmetrical, the disengagement results in spreading of the locking ring 52. The locking ring 52 is thereby clamped between the head of compression screw 50 and the bone plate 20. This results in fixing the compression screw 50 in place such that the compression screw 50 can not back out in axial direction. To remove the compression screw 50, compression screw 50 is rotated in the opposite direction. This results in the engagement of the saw blade geometries on the on the inner surface 56 of the locking ring 52 and the outer peripheral surface 60. Next, the compression screw 50 and the locking ring 52 may be removed simultaneously using the dedicated instrument.

Figure 6:
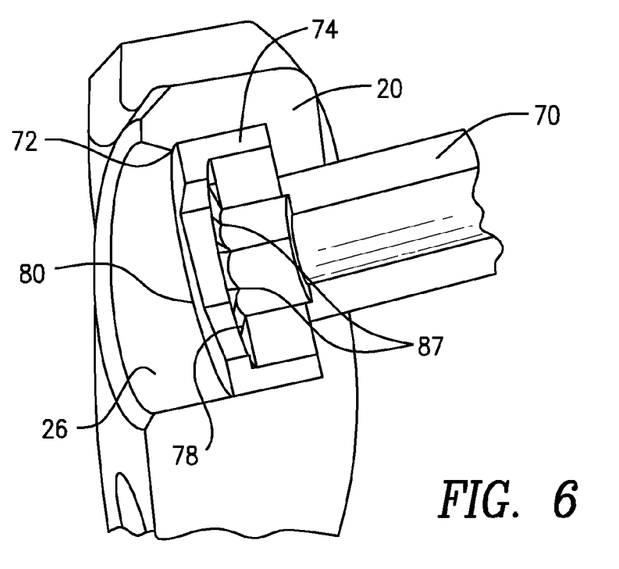
FIG. 6 is a sectional view of the bone plate of FIG. 1 with a second embodiment of a locking ring and a screw installed therein.
Figure 7:
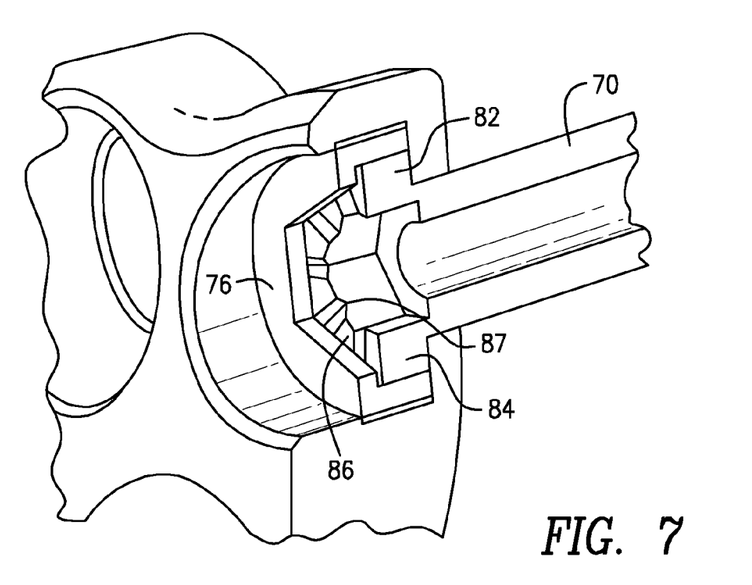
FIG. 7 is another sectional view of the embodiment of FIG. 6.

In yet another embodiment a compression screw 70 of a different design is used with a locking ring 72. FIGS. 6 and 7 show the bone plate 20, compression screw 70 and the locking ring 72 assembled together. The locking ring 72 has a threaded circular outer surface 74 that fits in the screw hole 26. The top wall 76 of the locking ring 72 projects towards the center of the screw hole 26 and has a hexagonal internal periphery. The bottom surface 78 of the top wall 76 has ridges 80. The compression screw 70 has a head 82 that has an outer peripheral surface 84 that slidably fits into the locking ring 72. The top surface 86 of the head of the compression screw 70 has depressions 87 that correspond to the ridges 80. Thus, when the compression screw 70 is assembled in locking ring 72, the ridges 80 sit in the depressions 87. The top surface 86 of the screw head 82 also has a hexagonal depression to allow engagement of a suitable screw driver. Other known shapes for the depression and corresponding screwdriver may also be used. The external surface of the locking ring 72 may have threads (not seen in the figures) that engage threads in the screw hole 26.

In use, the compression screw 70 and the locking ring 72 are assembled together and inserted into the screw hole 26. The assembly of the compression screw 70 and the locking ring 72 is then screwed into the bone using a dedicated insertion instrument that holds and rotates the compression screw 70 and the locking ring 72 simultaneously. When the head of the compression screw 70 reaches the terminal axial position in the screw hole 26, the compression screw 70 can be rotated further to apply compression to the fracture site. When the compression screw 70 is rotated further the ridges 80 loose contact with the depressions 87. This forms, for example, a small gap of approximately 0.1-0.4 millimeter between the compression screw 70 and the locking ring 72. As soon as the body weight is applied post-operatively, the femoral head fracture fragment presses the compression screw 70 back to the lateral side until the movement is stopped by the locking ring 72.

To remove the compression screw 70, compression screw 70 is rotated in the opposite direction. This results in the engagement of the ridges 80 in the depressions 87. Next the compression screw 70 and the locking ring 72 may be removed simultaneously using the dedicated instrument.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A method of fusing fractures of a femoral neck using a bone plate comprising the steps of:
   placing a bone plate on the femur;
   inserting an assembly of a bone screw and a locking ring in an opening in the plate;
   simultaneously threading the locking ring and the bone screw in the femur;
   threading the bone screw in the femur to compress the fracture;
   creating a space between the locking ring and the bone screw;
   allowing the bone screw to move towards the locking ring when the femur is loaded; and
   removing the locking ring and the bone screw by simultaneously rotating the locking ring and the bone screw using a dedicated instrument.

2. The method of claim 1, further comprising the step of; stopping further axial movement of the bone screw upon the screw head contacting the locking ring.

* * * * *